US007906661B2

(12) United States Patent
Naidu et al.

(10) Patent No.: US 7,906,661 B2
(45) Date of Patent: Mar. 15, 2011

(54) SEMI-SYNTHETIC CONVERSION OF PACLITAXEL TO DOCETAXEL

(75) Inventors: Ragina Naidu, Burnaby (CA); Samuel Siang Kiang Foo, Vancouver (CA); BaoYu Xue, Coquitlam (CA); Bo Fan, Vancouver (CA)

(73) Assignee: Chatham Biotec, Limited, Riverview, New Brunswick (CA)

( * ) Notice: Subject to any disclaimer, the term of this patent is extended or adjusted under 35 U.S.C. 154(b) by 78 days.

(21) Appl. No.: 11/631,466

(22) PCT Filed: Jun. 29, 2005

(86) PCT No.: PCT/US2005/023224
§ 371 (c)(1),
(2), (4) Date: Sep. 7, 2007

(87) PCT Pub. No.: WO2006/004898
PCT Pub. Date: Jan. 12, 2006

(65) Prior Publication Data
US 2008/0051590 A1    Feb. 28, 2008

(51) Int. Cl.
*C07D 305/00*    (2006.01)
(52) U.S. Cl. .......................................... 549/510; 549/511
(58) Field of Classification Search .................... 549/516
See application file for complete search history.

(56) References Cited

U.S. PATENT DOCUMENTS

| 5,319,112 | A | 6/1994 | Kingston et al. |
| 5,380,916 | A | 1/1995 | Rao |
| 5,530,020 | A | 6/1996 | Gunawardana et al. |
| 5,703,247 | A | 12/1997 | Kingston et al. |
| 5,808,113 | A | 9/1998 | Murray et al. |
| 6,136,989 | A | 10/2000 | Foo et al. |
| 6,197,981 | B1 | 3/2001 | Liu |
| 6,222,053 | B1 | 4/2001 | Zamir et al. |
| 6,576,777 | B2 | 6/2003 | Zamir et al. |
| 7,202,370 | B2 | 4/2007 | Naidu |
| 2001/0014746 | A1 | 8/2001 | Holton |
| 2001/0037020 | A1 | 11/2001 | Holton |
| 2001/0041803 | A1 | 11/2001 | Kasitu et al. |
| 2008/0033189 | A1 | 2/2008 | Naidu |
| 2008/0146824 | A1 | 6/2008 | Naidu et al. |
| 2008/0262250 | A1 | 10/2008 | Naidu |

FOREIGN PATENT DOCUMENTS

| EP | 1403261 | 3/2004 |
| WO | WO98/50378 | 11/1998 |
| WO | WO99/54322 | 10/1999 |
| WO | WO 2004/033442 A2 | 4/2004 |
| WO | WO2005/082875 | 9/2005 |

(Continued)

OTHER PUBLICATIONS

Nicolaou et al., "Chemistry and Biology of Taxol," *Angew. Chem. Int. Ed. Engl.* 33:15-44, 1994.

(Continued)

*Primary Examiner* — Janet L. Andres
*Assistant Examiner* — Raymond Covington
(74) *Attorney, Agent, or Firm* — Klarquist Sparkman, LLP (57) ABSTRACT

A process is provided for the semi-synthesis of taxane derivatives useful in the preparation of docetaxel, in particular, the semi-synthesis of protected taxane derivatives in a one pot reaction of protecting the C-2', C-7 and C-10 positions and introducing a t-Boc group at the nitrogen of the amide group at the C-3' position in paclitaxel and subsequently conversion to docetaxel, and derivatives used therein.

19 Claims, 1 Drawing Sheet

FOREIGN PATENT DOCUMENTS

| WO | WO2005/105767 | 11/2005 |
|---|---|---|
| WO | WO2005/118563 | 12/2005 |
| WO | WO2006/004708 | 1/2006 |

OTHER PUBLICATIONS

International Search Report dated Sep. 28, 2005 from PCT/US2005/019697.

International Search Report dated Nov. 28, 2005 from PCT/US2005/023224, filed on Jun. 29, 2005.

Beckvermit et al., "An Improved Method for Separating Paclitaxel and Cephalomannine Using Ozone and Girard Reagents," *J. Org. Chem.*, vol. 61, No. 25, pp. 9038-9040 (1996).

Chen et al., "Synthesis and Biological Evaluation of Novel C-4 Aziridine-Bearing Paclitaxel (Taxol) Analogs," CAPLUS 123:112445, Abstract Only, *Journal of Medicinal Chemistry*, vol. 38, No. 12, pp. 2263-2267 (1995).

Commerçon et al., "Improved Protection and Esterification of a Precursor of the TAXOTERE® and Taxol Side Chains," *Tetrahedron Letters*, vol. 33, No. 36, pp. 5185-5188 (1992).

Final Office action from the U.S. Patent and Trademark Office in U.S. Appl. No. 11/587,407, dated Apr. 16, 2009.

Gennari et al., "Computer-Assisted Design and Synthetic Applications of Chiral Enol Borinates: Novel, Highly Enantioselective Aldol Reagents," *J. Braz. Chem. Soc.*, vol. 9, No. 4, pp. 319-326 (1998).

Gennari et al., "Rationally designed chiral enol Borinates: Powerful reagents for the stereoselective synthesis of natural products," *Pure & Appl. Chem.*, vol. 69, No. 3, pp. 507-512 (1997).

International Search Report for PCT/US2005/014080 (mailed Aug. 3, 2005).

International Search Report for PCT/US2005/005953 (mailed Sep. 14, 2005).

Kanazawa et al., "Highly Stereocontrolled and Efficient Preparation of the Protected, Esterification-Ready Docetaxel (Taxotere) Side Chain," *Journal of Organic Chemistry*, vol. 59, pp. 1238-1240 (1994).

Klein, L., "Synthesis of 9-Dihydrotaxol: A Novel Bioactive Taxane," *Tetrahedron Letters*, vol. 34, No. 13, pp. 2047-2050 (Mar. 26, 1993).

Notice of Allowance from the U.S. Patent and Trademark Office in U.S. Appl. No. 11/587,407, dated Jul. 22, 2010.

Office Action from European Patent Office in European Patent Application No. 05760288.0, dated Jul. 23, 2009.

Office action from the U.S. Patent and Trademark Office in U.S. Appl. No. 10/590,647, dated Sep. 19, 2008.

Office action from the U.S. Patent and Trademark Office in U.S. Appl. No. 11/587,407, dated Sep. 25, 2008.

Office action from the U.S. Patent and Trademark Office in U.S. Appl. No. 11/587,407, dated Nov. 27, 2009.

Office action from the U.S. Patent and Trademark Office in U.S. Appl. No. 11/628,428, dated Sep. 4, 2009.

Office action from the U.S. Patent and Trademark Office in U.S. Appl. No. 11/628,428, dated Feb. 3, 2010.

Pines et al., "The Stereochemistry of 2,3-Diphenyl-1-methylpropylamine," *Journal of Medical Chemistry*, vol. 10, No. 4, pp. 725-728 (1967).

Rimoldi et al., "An Improved Method for the Separation of Paclitaxel and Cephalomannine," *Journal of Natural Products*, vol. 59, No. 2, pp. 167-168 (1996).

FIGURE 1

SEMI-SYNTHETIC CONVERSION OF PACLITAXEL TO DOCETAXEL

CROSS REFERENCE TO RELATED APPLICATIONS

This is the U.S. National Stage of International Application No. PCT/US2005/023224, filed Jun. 29, 2005, which was published in English under PCT Article 21(2), which claims the benefit of U.S. patent application Ser. No. 10/881,711, filed Jun. 29, 2004.

BACKGROUND OF THE INVENTION

1. Field of the Invention

The present invention relates to a semi-synthesis of taxane derivatives useful in the preparation of docetaxel, from pure or crude paclitaxel or related taxane starting material, in particular, the semi-synthesis of protected taxane derivatives in a one pot reaction and its conversion to docetaxel.

2. Description of the Related Art

The taxane family of terpenes has received much attention in the scientific and medical community because the members of this family have demonstrated broad spectrum anti-leukemic and tumor-inhibitory activity. Docetaxel (1, Taxotere), a semi-synthetic analog, and paclitaxel (2, Taxol), a complex diterpene isolated from the bark of the Pacific yew tree (*Taxus brevifolia*) are arguably the most outstanding cancer chemotherapeutic substances discovered in recent times. For example, paclitaxel has been found to have activity against different forms of leukemia and against solid tumors in the breast, ovary, brain, and lung in humans. While paclitaxel can be obtained from the yew tree or semi-synthetically, only the latter option is currently available for the formation of non-natural docetaxel. The partial synthesis of this important compound has generally been accomplished through esterification of a derivative of the (2R,3S)phenylisoserine side chain with a protected form of 10-deacetylbaccatin III, a comparatively abundant natural product also present in the yew tree.

TAXOTERE (1)

TAXOL (2)

As disclosed in U.S. Pat. No. 4,814,470, taxotere has been found to have very good anti-tumor activity and better bio-availability than paclitaxel. Taxotere is similar in structure to paclitaxel, having t-butoxycarbonyl instead of benzoyl on the amino group at the 3' position, and a hydroxy group instead of the acetoxy group at the C-10 position.

Docetaxel and paclitaxel may be prepared semi-synthetically from 10-deacetylbaccatin III or baccatin III as set forth in U.S. Pat. Nos. 4,924,011 and 4,924,012, by the reaction of a β-lactam and a suitably protected 10-deacetylbaccatin III or baccatin III derivative as set forth in U.S. Pat. No. 5,175,315, by a method using an oxazoline compound as set forth in International Patent Kokai No. Hei 7-504444, by a method using thioester compound as set forth in International Patent Kokai No. Hei 10-505360 or by a method using cinnamic acid as set forth in Tetrahedron, Vol. 42, p. 4451,1986, etc. 10-deacetylbaccatin III (10-DAB, 3) and Baccatin III (4) can be separated from mixtures extracted from natural sources such as the needles, stems, bark or heartwood of numerous *Taxus* species and have the following structures.

10 DAB (3)

BACC III (4)

Although much of the research towards the semi-synthesis of paclitaxel and taxotere has involved 10-deacetylbaccatin III as the starting material, other taxanes from the *Taxus* species, such as 9-dihydro-13-acetylbaccatin III (9-DHB, 5), present in the Canadian yew (*Taxus Canadensis*), cephalomannine (6), 10-deacetyl taxol (10-DAT, 7), 7-xylosyl taxol (8), 10-deacetyl-7-xylosyl taxol (9) and a number of 7-epi-taxanes have been collected and identified.

9-DHB (5)

CEPHALOMANNINE

10-DAT

7-XYLOSYL TAXOL

10-DEACETYL-7-XYLOSYL TAXOL

As disclosed in U.S. patent application Ser. No. 10/695,416, which application is assigned to the assignee of the present invention, docetaxel and paclitaxel may also be prepared semi-synthetically from 9-dihydro-13-acetylbaccatin III.

However, the above methods thus far developed involve subjects such as reaction under the conditions of extremely low temperatures, generation of diastereomers, use of asymmetry controlling agents, and the reaction under strongly alkaline conditions, which cause problems upon the industrialization thereof.

Accordingly, there remains a need for new and improved processes for the preparation of taxane derivatives and their conversion to docetaxel, and also for the preparation of such taxane intermediates from crude and partially purified mixtures comprising a plurality of taxanes. The present invention addresses these needs and provides further related advantages.

BRIEF SUMMARY OF THE INVENTION

The present invention provides a simple process for conversion of paclitaxel or a paclitaxel-containing material to its synthetic analog—docetaxel. Accordingly, one embodiment of the present invention provides a process for producing a taxane intermediate under mild conditions using a pure or partially purified paclitaxel or a paclitaxel analog as a starting material, the taxane intermediate can later be used as a precursor to docetaxel. The process comprises protecting a compound of Formula (I):

(I)

wherein, $R^1$ is alkyl, alkenyl or aryl; and X, Y and Z are the same or different and independently hydroxy or protected hydroxy. In particular, the process comprises: protecting one or more hydroxy groups at the C-2', C-7 and C-10 positions of the taxane; and introducing a t-Boc group at the nitrogen of the amide group at the C-3' position of the taxane to provide a C-2', C-7, C-10 and N-t-Boc protected paclitaxel derivative, wherein the steps of protecting one or more hydroxy groups and introducing the t-Boc group comprises combining, in a one pot reaction, the taxane with a hydroxy protecting group and a t-Boc agent.

In another embodiment, the hydroxy protecting groups at the C-2', C-7 and C-10 positions can be the same or different.

In another embodiment, the step of protecting one or more hydroxy groups at the C-2', C-7 and C-10 positions of the taxane is carried out in the presence of a base.

In yet another embodiment, the step of protecting one or more hydroxy groups at the C-2', C-7 and C-10 positions of the taxane is carried out in the presence of an acid.

A further embodiment of the present invention provides a process for preparing docetaxel from a taxane of Formula (I):

(I)

wherein, $R^1$ is alkyl, alkenyl or aryl; and X, Y and Z are the same or different and independently hydroxy or protected hydroxy, the process comprising: protecting one or more hydroxy groups at the C-2', C-7 and C-10 positions of the taxane; introducing a t-Boc group at the nitrogen of the amide group at the C-3' position of the taxane to provide a protected paclitaxel derivative having an urea linkage at the C-3' position; selectively removing the —C(O)$R^1$ group from the urea linkage to provide a protected docetaxel; and converting the protected docetaxel to docetaxel by removing the hydroxy-protecting groups at the C-2', C-7 and C-10 positions, wherein the step of protecting one or more hydroxy groups at C-2', C-7 and C-10 positions, and introducing the t-Boc group at the nitrogen site of the amide group of the taxane comprises combining, in a one pot reaction, the taxane of Formula (I) with a hydroxy protecting agent and a t-Boc agent, and wherein the step of selectively removing the —C(O)$R^1$ group comprises subjecting the protected paclitaxel derivative having the urea linkage to a first base.

In another embodiment, the hydroxy protecting groups at the C-2', C-7 and C-10 positions can be the same or different.

In another embodiment, the step of protecting one or more hydroxy groups at the C-2', C-7 and C-10 positions of the taxane is carried out in the presence of a second base.

In yet another embodiment, the step of protecting one or more hydroxy groups at the C-2', C-7 and C-10 positions of the taxane is carried out in the presence of an acid.

In addition, the present invention provides a simplified and efficient process for preparing docetaxel from an initial mixture of taxanes, wherein the initial mixture comprises paclitaxel and at least one additional taxane selected from the group of 10-deacetylbaccatin III, 9-dihydro-13-acetylbaccatin III, baccatin III, cephalomannine, 10-deacetyl taxol, 7-xylosyl taxol and 10-deacetyl-7-xylosyl taxol, the process comprising the steps of: protecting the hydroxy groups at the C-2' and C-7 positions of paclitaxel; introducing a t-Boc group at the nitrogen of the amide group at the C-3' position of paclitaxel to provide a protected paclitaxel derivative having an urea linkage at the C-3' position; selectively removing the benzoyl group from the urea linkage to provide a protected docetaxel; and converting the protected docetaxel to docetaxel by removing the hydroxy-protecting groups at the C-7, C-2' and C-10 positions, wherein the step of protecting the hydroxy groups at C-2' and C-7 positions, and introducing a t-Boc group at the nitrogen site of the amide group of paclitaxel are carried out in a one pot reaction wherein the mixture containing paclitaxel is combined with a hydroxy protecting agent and a t-Boc agent; and wherein the step of selectively removing the benzoyl group comprises subjecting the protected paclitaxel derivative having the urea linkage to a first base.

In another embodiment, the step of protecting the hydroxy group at the C-2' and C-7 position of paclitaxel further comprises protecting one or more hydroxy groups at the C-2', C-7 and C-10 positions of each taxane in the initial mixture having a hydroxy group at these positions.

Another embodiment of the present invention provides a process of converting a taxane of Formula (I)

wherein, $R^1$ is alkyl, alkenyl or aryl, and X, Y and Z are the same or different and independently hydroxy or protected hydroxy, to docetaxel, via a primary amine intermediate. The process comprises: introducing a nitroso group (—NO) at the nitrogen of the amide group at the C-3' position of the taxane to provide a N-nitrosoamide intermediate; hydrolyzing the N-nitrosoamide intermediate to provide a N-nitrosoamine intermediate; reducing the N-nitrosoamine intermediate to provide a primary amine intermediate; and converting the primary amine derivative to docetaxel, These and other aspects of the invention will be apparent using chemical reactions that are mild, efficient and selective as described herein, upon reference to the attached figures and following detailed description.

DETAILED DESCRIPTION OF THE INVENTION

As mentioned above, the present invention relates to processes for converting paclitaxel, paclitaxel containing material or other paclitaxel derivatives to docetaxel.

I. DEFINITIONS

As used herein, the following terms have the following meanings.

"Silica matrix" is a solid media containing a silicate which is used as an adsorbent or column material in chromatographic separations, including (but not limited to) ordinary silica, Florisil, porous silica gels or any physical formulation of a silicate for use in chromatographic procedures.

"Taxane-containing material" refers to selected parts of a plant, plant tissues, cell cultures, microorganisms or extracts with extractable taxanes, including paclitaxel, 10-deacetylbaccatin III (10-DAB), baccatin III (BACC III), 9-dihydro-13-acetylbaccatin III (9-DHB), cephalomannine, 10-deacetyl taxol (10-DAT), 7-xylosyl taxol and 10-deacetyl-7-xylosyl taxol.

"Crude taxane extract" refers to a composition obtained from a taxane-containing material by treating the taxane-containing material with at least one solvent.

"Partially purified taxane extract" refers to a paclitaxel enriched composition obtained from the chromatographic separation and/or recrystallization of a crude or partially purified taxane extract.

"Waste stream fractions" refers to fractions collected following the chromatographic separation and collection of paclitaxel enriched fractions from a crude or partially purified taxane extract by, for example, the process of U.S. Pat. No. 6,136,989.

"Waste mother liquors" refers to mother liquors collected following the recrystallization of a crude or partially purified taxane extract by, for example, the process of U.S. Pat. No. 6,136,989.

"Hydroxy-protecting group" refers to any derivative of a hydroxy group known in the art which can be used to mask the hydroxy group during a chemical transformation and later removed under conditions resulting in the hydroxy group being recovered without other undesired effects on the remainder of the molecule. Many esters, acetals, ketals and silyl ethers are suitable protecting groups. Examples of hydroxy-protecting groups include, without limitation, formyl, acetyl (Ac), benzyl (PhCH$_2$), 1-ethoxyethyl (EE), methoxymethyl (MOM), (methoxyethoxy)methyl (MEM), (p-methoxyphenyl)methoxymethyl (MPM), tert-butyldimethylsilyl (TBS), tert-butyldiphenylsilyl (TBPS), tert-butoxycarbonyl (tBoc, t-Boc, tBOC, t-BOC), tetrahydropyranyl (THP), triphenylmethyl (Trityl, Tr), 2-methoxy-2-methylpropyl, benzyloxycarbonyl (Cbz), dichloroacetyl, trichloroacetyl (OCCCl$_3$), 2,2,2-trichloroethoxycarbonyl (Troc), benzyloxymethyl (BOM), tert-butyl (t-Bu), triethylsilyl (TES), trimethylsilyl (TMS), triisopropylsilyl (TIPS), propionyl, isopropionyl, pivalyl, dimethylisopropylsilyl, diethylisopropylsilyl, methyldiphenylsilyl, dimethylphenylsilyl, tert-butyldiphenylsilyl, tribenzylsilyl, triphenylsilyl, trichloroethoxycarbonyl, benzyl, para-nitrobenzyl, para-methoxybenzyl, benzoyl, methoxyethyl, para-methoxyphenyl, tetrahydrofuranyl, alkylsulfonyl and arylsulfonyl. The related term "protected hydroxy group" or "protected —OH" refers to a hydroxy group that is bonded to a hydroxy-protecting group. General examples of protected hydroxy groups include, without limitation, —O-alkyl, —O-acyl, acetal, and —O-ethoxyethyl (OEE), where some specific protected hydroxy groups include, formyloxy, acetoxy, propionyloxy, chloroacetoxy, bromoacetoxy, dichloroacetoxy, trichloroacetoxy, trifluoroacetoxy, methoxyacetoxy, phenoxyacetoxy, benzoyloxy, benzoylformoxy, p-nitro benzoyloxy, ethoxycarbonyloxy, methoxycarbonyloxy, propoxycarbonyloxy, 2,2,2-trichloroethoxycarbonyloxy, benzyloxycarbonyloxy, tert-butoxycarbonyloxy, 1-cyclopropylethoxycarbonyloxy, phthaloyloxy, butyryloxy, isobutyryloxy, valeryloxy, isovaleryloxy, oxalyoxy, succinyloxy and pivaloyloxy, phenylacetoxy, phenylpropionyloxy, mesyloxy, chlorobenzoyloxy, para-nitrobenzoyloxy, para-tert-butyl benzoyloxy, capryloyloxy, acryloyloxy, methylcarbamoyloxy, phenylcarbamoyloxy, naphthylcarbamoyloxy, and the like. The related term "hydroxy protecting agent" refers to a reagent that introduces a hydroxy protecting group to a free hydroxy functionality. Typically, a hydroxy protecting agent comprises a hydroxy protecting group as those listed above and a leaving group, such as a halide or a triflate. When the hydroxy protecting group is an alkyl, the hydroxy protecting agent is referred herein as an alkylating agent. The alkyl moiety of the alkylating agent can be optionally substituted by aryl, alkoxy, or aryloxy. Suitable alkylating agent includes benzyl bromide, benzyl chloride, methoxymethyl chloride, ethyl vinyl ether, and benzyloxymethyl chloride. Similarly, when the hydroxy protecting group is an acyl or silyl, the hydroxy protecting agent can be referred herein as an acylating agent or silylating agent, respectively. Suitable acylating agent includes, but not limited to, Boc$_2$O and acetoxyacetyl chloride. Suitable silylating agents includes TMSCl (trimethylsilyl chloride), TESCl (triethylsilyl chloride), etc. More exemplary hydroxy-protecting groups and hydroxy protecting agents are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

"Thiol-protecting group" refers to any derivative of a thiol group known in the art which can be used to mask the thiol group during a chemical transformation and later removed under conditions resulting in the thiol group being recovered without other undesired effects on the remainder of the molecule. Examples of thiol-protecting groups include, without limitation, triphenylmethyl (trityl, Trt), acetamidomethyl (Acm), benzamidomethyl, 1-ethoxyethyl, benzoyl, and the like. The related term "protected thiol group" refers to a thiol group that is bonded to a thiol-protecting group. General examples of protected thiol groups include, without limitation, —S-alkyl (alkylthio, e.g., $C_1$-$C_{10}$alkylthio), —S-acyl (acylthio), thioacetal, —S-aralkyl (aralkylthio, e.g., aryl($C_1$-$C_4$)alkylthio), where some specific protected thiols groups include methylthio, ethylthio, propylthio, isopropylthio, butylthio, isobutylthio, sec-butylthio, tert-butylthio, pentylthio, isopentylthio, neopentylthio, hexylthio, heptylthio, nonylthio, cyclobutylthio, cyclopentylthio and cyclohexylthio, benzylthio, phenethylthio, propionylthio, n-butyrylthio and iso-butyrylthio. Thiol-protecting groups and protected thiol groups are described in, e.g., C. B. Reese and E. Haslam, "Protective Groups in Organic Chemistry," J. G. W. McOmie, Ed., Plenum Press, New York, N.Y., 1973, Chapters 3 and 4, respectively, and T. W. Greene and P. G. M. Wuts, "Protective Groups in Organic Synthesis," Second Edition, John Wiley and Sons, New York, N.Y., 1991, Chapters 2 and 3.

The following Table shows the chemical structures of some protecting groups, as well as the nomenclatures used to identify these chemical structures.

TABLE 1

TABLE 1-continued

| | | | |
|---|---|---|---|
| Triethylsilyl (TES) |  | Triethylsiloxy (—OTES) |  |
| Benzoyl |  | Benzoyloxy |  |
| t-Butyloxycarbonyl (tBOC) |  | | |
| t-Butyloxycarbonyl (—O-tBOC) |  | | |
| para-Methoxyphenyl (PMP) |  | | |

"Alkyl" refers to an optionally substituted hydrocarbon structure, containing no saturation, wherein the carbons are arranged in a linear, branched or cyclic manner, including combinations thereof. Lower alkyl refers to alkyl groups of 1 to 5 carbon atoms. Examples of lower alkyl groups include methyl, ethyl, propyl, isopropyl, butyl, s- and t-butyl and the like. "Cycloalkyl" is a subset of alkyl and includes mono or bi-cyclic hydrocarbon groups of from 3 to 13 carbon atoms. Examples of cycloalkyl groups include cyclopropyl, cyclobutyl, cyclopentyl, norbornyl, adamantyl and the like. When an alkyl residue having a specific number of carbons is named, all geometric isomers having that number of carbons are intended to be encompassed; thus, for example, "butyl" is meant to include n-butyl, sec-butyl, isobutyl and t-butyl; propyl includes n-propyl and isopropyl.

"Alkenyl" refers to an optionally substituted alkyl group having at least one site of unsaturation, i.e., at least one double bond.

"Alkynyl" refers to an optionally substituted alkyl group having at least one triple bond between two adjacent carbon atoms.

"Alkoxy" refers to a radical of the formula —O-alkyl. Examples include methoxy, ethoxy, propoxy, isopropoxy, cyclopropyloxy, cyclohexyloxy and the like. Lower-alkoxy refers to groups containing one to five carbons.

"Alkoxycarbonyl" refers to a radical of the formula —C(O)-alkoxy, wherein alkoxy is as defined herein.

"Aryl" refers to optionally substituted phenyl or naphthyl. Exemplary substituents for aryl include one or more of halogen, hydroxy, alkoxy, aryloxy, heteroaryloxy, amino, alkylamino, dialkylamino, mercapto, alkylthio, arylthio, heteroarylthio, cyano, carboxyl, alkoxycarbonyl where the alkoxy portion contains 1 to 15 carbons, aryloxycarbonyl where the aryloxy portion contains 6 to 20 carbon, or heteroarylcarbonyl where the heteroaryl portion contains 3 to 15 carbon atoms.

"Aryloxy" refers to a radical of the formula —O-aryl, wherein aryl is defined as above. Representative aryloxy includes phenoxy.

"Aryloxycarbonyl" refers to a radical of the formula —C(O)-aryloxy, wherein aryloxy is as defined herein.

"Heteroaryl" refers to an optionally substituted 5- or 6-membered heteroaromatic ring containing 1-3 heteroatoms selected from O, N or S; a bicyclic 9- or 10-membered heteroaromatic ring system containing 1-3 heteroatoms selected from O, N or S; or a tricyclic 13- or 14-membered heteroaromatic ring system containing 1-3 heteroatoms selected from O, N or S. Exemplary aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

"Heterocycle" means a 5- to 7-membered monocyclic, or 7- to 10-membered bicyclic, heterocyclic ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring. The heterocycle may be optionally substituted with 1-5 substituents. The heterocycle may be attached via any heteroatom or carbon atom. Heterocycles include heteroaryls as defined above. Thus, in addition to the heteroaryls listed above, heterocycles also include morpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Acyl" refers to a radical of the formula —C(=O)—R, wherein R is alkyl, alkenyl, alkynyl, aryl, alkoxy, aryloxy, heterocycle or heteroaryl, where alkyl, alkenyl, alkynyl, aryl, alkoxy, aryloxy, heterocycle and heteroaryl are as defined herein. Representative acyl groups include acetyl, benzoyl, propionyl, isobutyryl, t-butoxycarbonyl, and the like. Lower-acyl refers to groups containing one to five carbons.

"Leaving group" refers to a chemical moiety that may be displaced during a substitution or elimination reaction. Exemplary leaving groups include halogen (e.g., bromide and chloride), triflate and tosyl.

"Halogen" refers to fluoro, chloro, bromo or iodo.

"Oxo" refers to =O.

"Hydrocarbonyl" refers to alkyl, alkenyl, alkynyl or aryl.

"Metal alkoxide" refers to a base of a general formula MO-alkyl, wherein M is a Group I, II, III or transition metal. Representative metal alkoxides are lithium t-butoxide, sodium t-butoxide, potassium t-butoxide, calcium methoxide, lithium methoxide.

"Metal hydroxide" refers to a base of a general formula M-OH, wherein M is a Group I, II, III or transition metal. Representative metal hydroxide are lithium hydroxide (LiOH), sodium hydroxide (NaOH), calcium hydroxide (Ca(OH)$_2$).

The term "substituted" as used herein means any of the above groups (e.g., alkyl, alkoxy, acyl, aryl, heteroaryl and heterocycle) wherein at least one hydrogen atom is replaced with a substituent. In the case of an oxo substituent ("=O") two hydrogen atoms are replaced. Substituents include halogen, hydroxy, oxo, alkyl, aryl, alkoxy, aryloxy, acyl, mercapto, cyano, alkylthio, arylthio, heteroarylthio, heteroaryl, heterocycle, —NR$_a$R$_b$, —NR$_a$C(=O)R$_b$, —NR$_c$C(=O) NR$_a$R$_b$, —NR$_a$C(=O)OR$_b$, —NR$_a$SO$_2$R$_b$, —C(=O) NR$_a$R$_b$, —OC(=O)R$_a$, —OC(=O)OR$_a$, —OC(=O) NR$_a$R$_b$, —NR$_a$SO$_2$R$_b$ or a radical of the formula —Y—Z—R$_a$ where Y is alkanediyl, substituted alkanediyl or a direct bond, alkanediyl refers to a divalent alkyl with two hydrogen atoms taken from the same or different carbon atoms, Z is —O—, —S—, —S(=O)—, —S(=O)$_2$-, —N(R$_b$)—, —C(=O)—, —C(=O)O—, —OC(=O)—, —N(R$_b$)C (=O)—, —C(=O)N(R$_b$)— or a direct bond, wherein R$_a$, R$_b$ and R$_c$ are the same or different and independently hydrogen, amino, alkyl, substituted alkyl (including halogenated alkyl), aryl, substituted aryl, heteroaryl, substituted heteroaryl, heterocycle or substituted heterocycle or wherein R$_a$ and R$_b$ taken together with the nitrogen atom to which they are attached form a heterocycle or substituted heterocycle.

The term "one pot reaction", (also referred to herein as a "one pot synthesis") refers to a multi-step chemical reaction carried out in a reaction vessel. Typically, a reaction intermediate is generated in an initial step of reaction, the intermediate is then reacted in situ with other component(s) present in or introduced to the same vessel. The reaction intermediate generated is not isolated but serves directly as a reactant in a next step of reaction. For example, in one embodiment of the instant invention, one or more free hydroxy groups of a taxane (e.g., paclitaxel) are protected, the protected taxane intermediate is not isolated and is used directly in a next step of N-acylation whereby a t-butoxycarbonyl (t-Boc) group is attached to the nitrogen of the amide group at the C-3' position.

II. PROCESS FOR PROTECTING A PACLITAXEL OR A RELATED TAXANE THEREOF

As noted above, the present invention relates to a semi-synthesis of paclitaxel derivatives useful in the preparation of docetaxel. In particular, one embodiment of the present invention provides a process comprising protecting one or more of the free hydroxy groups at any of the C-7, C-10 and C-2' positions, and introducing a t-Boc group at the nitrogen of the amide group at the C-3' position of a compound of Formula (I) to provide a protected paclitaxel derivative having an urea linkage therein. One embodiment provides a process of protecting the hydroxy group(s) and introducing the t-Boc group, the process comprising, in one reaction vessel, combining a compound of Formula (I) with a base, a hydroxy protecting agent and a t-Boc agent. The phrase "t-Boc agent" as used herein refers to a reagent that introduces a t-Boc group to the nitrogen of the amide group at the C-3' position, in other words, the t-Boc agent further acylates the nitrogen of the amide group. Suitable "t-Boc agent" can be the same as those hydroxy protecting agents having a t-Boc moiety, for example, Boc$_2$O. The t-Boc agent is selected to react with the amide group in the presence of a base after the reactive hydroxy groups at the C-2', C-7 and/or C-10 positions have been protected. Reaction Scheme 1 is shown below to illustrate this process:

wherein,

R$^1$ is alkyl, alkenyl or aryl;

R$^2$, R$^3$ and R$^4$ are the same or different and independently a hydroxy protecting group; and X, Y and Z are the same or different and independently hydroxy or protected hydroxy.

The protecting step provides protection to one or more reactive hydroxy groups in a compound of Formula (I). In one embodiment, when X and Z are free hydroxy groups, as in paclitaxel (2) or cephalomannine (6), the protection step comprises protecting the hydroxy groups at both the C-7 and C-2' positions. In another embodiment, X, Y and Z are all free hydroxy groups, as in 10-DAT (7), the protection step comprises protecting all three hydroxy groups at C-2', C-7 and C-10 positions. In yet another embodiment, X and Y are free hydroxy, and Z is already a protected hydroxy, as in 10-deacetyl-7-xylosyl taxol (9), the protection step comprises protecting the free hydroxy groups at C-2' and C-10 positions.

In one embodiment, the same hydroxy protecting agent is used to protect all the available reactive hydroxy groups. In another embodiment, different hydroxy protecting agents can be used to protect the C-2', C-7 and/or C-10 positions. Typically, the free hydroxy group at the C-2' position is more reactive than the hydroxy group at the C-7, which is in turn more reactive than the hydroxy group at the C-10 positions. This leads to the preferential protection whereby the hydroxy group at C-2' will be protected first, followed by those at the C-7 and C-10 positions. Thus, it is possible that the hydroxy protecting step comprises sequential steps of protecting the C-2', C-7 and C-10 positions, with a different protecting agent for each step. For example, C-2' can be protected, using about one equivalent of a first hydroxy protecting agent, followed by the protection of the C-7 position using a second hydroxy protecting agent and, if necessary, followed by the protection of the C-10 position using a third protecting agent. The reaction can be carried out in the same reaction vessel without isolating any of the protected intermediates.

In a further embodiment, it is possible that the hydroxy protecting agent is the same as the t-Boc agent. For example, $Boc_2O$ can be employed as a hydroxy protecting agent to protect, where appropriate, one or more of the reactive hydroxy groups at any of the C-2', C-7 and C-10 positions. After the protection is completed, without isolating the protected taxane intermediate, $Boc_2O$ can be used to introduce a t-Boc group to the nitrogen of the amide group at the C-3' position in the presence of a base.

The foregoing steps of protecting hydroxy groups and introducing the t-Boc group are further described below in details.

General Method of Protection

The hydroxy groups at the C-2', C-7 and/or C-10 positions of a taxane of Formula (I) can be selectively protected using any of a variety of hydroxy protecting agents, such as silylating, acylating, alkylating agents and those agents forming acetal and ketal with the hydroxy group. The hydroxy protecting step can be carried out in the presence of a base or an acid, depending on the hydroxy protecting agent(s) used.

One embodiment of the present invention provides the protection of one or more hydroxy groups at the C-2', C-7 and/or C-10 in the presence of a base. Formula (I) is:

(I)

wherein, $R^1$ is alkyl, alkenyl or aryl; and

X, Y and Z are the same or different and independently hydroxy or protected hydroxy.

In particular, the C-2', C-7 and/or C-10 hydroxy group may be silylated using any of a variety of common silylating agents including, but not limited to, tri(hydrocarbonyl)silyl halides and tri(hydrocarbonyl)silyl triflates. The hydrocarbonyl moieties of these compounds may be optionally substituted and preferably are substituted or unsubstituted alkyl or aryl. Representative silylating agents include, tribenzylsilyl chloride, trimethylsilyl chloride, triethylsilyl chloride, dimethylisopropylsilyl chloride, dimethylphenylsilyl chloride and the like.

Alternatively, selective acylation of the C-2', C-7 and/or C-10 hydroxy group can be achieved using any of a variety of common acylating agents, but not limited to substituted and unsubstituted carboxylic acid derivatives, e.g., carboxylic acid halides, anhydrides, dicarbonates, isocyanates and haloformates. Representative acylating agents include, di-tert-butyl dicarbonate ($Boc_2O$), dibenzyl dicarbonate, diallyl dicarbonate, 2,2,2-trichloroethyl chloroformate, benzyl chloroformate, dichloroacetyl chloride, acetyl chloride or another common acylating agent.

Alternatively, selective alkylation of the C-2', C-7 and/or C-10 hydroxy group can be achieved using any of a variety of common alkylating agents, such as benzyl chloride and benzyl bromide.

According to the present invention, the protecting step is carried out in the presence of a base, such as, for example, DMAP, pyridine, TEA, LiOH, Li-t-OBu, n-BuLi, LiH, LiHMDS, KHMDS, K-t-OBu, NaH, NaHMDS, Na-t-OBu and mixtures of any two or more of the foregoing, such as a mixture of n-BuLi/Li-t-OBu, and the hydroxy-protecting group is an alkylating agent, silylating agent or acylating agent.

Exemplary reaction conditions are as follows: a taxane of Formula (I), or a mixture of taxanes, is dissolved in an organic solvent, such as anhydrous DCM (dichloromethane) or THF (tetrahydrofuran) or DMF (dimethyl formamide) or DMSO (dimethyl sulfoxide) or acetonitrile under an argon atmosphere at low to around room temperature. To this solution is added DMAP (dimethylaminopyridine) or any of the lithium, sodium or potassium base, such as Li-t-OBu, K-t-OBu, n-BuLi, a mixture of n-BuLi/K-t-OBu or LiOH, followed by an hydroxy protecting agent, such as an acylating agent (e.g., di-tert-butyl dicarbonate), or an silylating agent (e.g., triethyl silyl chloride) or any other hydroxy-protecting agents as described herein. The mixture is left at low to around room temperature until complete consumption of the starting material, as visualized by TLC to afford a C-7, C-2' and/or C-10 protected taxane or a mixture of C-7, C-2' and/or C-10 protected taxanes. "Low temperature" as used herein refers to temperature between −78° C. to room temperature.

As noted above, the protecting step can be carried out using the same hydroxy protecting agent for all the available reactive hydroxy groups at the C-2', C-7 and/or C-10 positions, or using different hydroxy protecting agent for each of the hydroxy groups to be protected. In light of the different reactivities of the hydroxy groups at the C-2, C-7 and C-10 positions as described above, one skilled in the art will readily appreciate that by controlling the equivalency of a hydroxy protecting agent in each step, C-2', C-7 and/or C-10 can be protected by different hydroxy protecting groups.

Another embodiment of the present invention provides the protection of one or more hydroxy groups at the C-2', C-7 and/or C-10 in the presence of a catalytic amount of an acid. Formula (I) is:

(I)

wherein, $R^1$ is alkyl, alkenyl or aryl; and

X, Y and Z are the same or different and independently hydroxy or protected hydroxy.

In particular, the C-2', C-7 and/or C-10 hydroxy group may be alkylated with an alkylating agent such as ethyl vinyl ether and methoxymethyl chloride. Suitable acid includes p-toluenesulfonic acid and other protic acid. Protic acid refers to an acid that yields an H+ ion. Only catalytic amount of the acid is needed to initiate the protecting step. Typically, less than 1 equivalent of the acid is used, more typically, less than 0.5 equivalent of the acid is used, more typically, less than 0.2 equivalent of the acid is used.

It is possible that one hydroxy group is protected in the presence of an acid, while the others are protected in the presence of a base. For example, C-2' paclitaxel can be first protected using about one equivalent of ethyl vinyl ether in the presence of a catalytic amount of p-toluenesulfonic acid. Without isolating the C-2' protected paclitaxel (i.e., 2'-OEE paclitaxel), a base and another hydroxy protecting agent are added. Advantageously, the amount of the base used is selected with the expectation that some of it will be consumed by the acid that might still be present in the reaction mixture. In any event, one skilled in the art will readily appreciate that all the reactive hydroxy groups of a taxane of Formula (I) are to be protected by the same or different hydroxy protecting groups.

Following protection of the hydroxy groups at the C-7, C-2' and/or C-10 positions of a taxane using the foregoing process, the introduction of a t-Boc group at the nitrogen of the amide group of the taxane may be performed in the same vessel without isolating the product of the hydroxy-protecting step according to the following method.

General Method of Introducing t-BOC at the Nitrogen of the Amide Group

The introduction of a tert-butoxycarbonyl (t-Boc) to the above protected taxane is also referred herein as a N-acylation step, whereby a t-Boc group replaces the hydrogen of the —NHC(O)R$^1$ group to provide a taxane intermediate having an urea linkage at the C-3' position, as represented by Formula (II) in Reaction Scheme 1. According to the present invention, the N-acylation step is carried out in a combined step by adding to the hydroxy-protected taxane in the same reaction vessel, a base and a t-Boc agent. Representative bases include DMAP, TEA, LiOH, n-BuLi, LiH, LiHMDS, KHMDS, NaH, NaHMDS or a mixture of any two or more of the foregoing. In addition, the combined step may further comprise combining the taxane with a metal alkoxide, wherein the metal is selected from the group consisting of Group I, II and III metals and transition metals. Representative metal alkoxide includes, but is not limited to Li-t-Bu, Na-t-Bu and K-t-Bu. Representative t-Boc agent includes, but is not limited to, Boc$_2$O.

An exemplary reaction condition for introducing the t-Boc group includes, dissolving a C-7, C-2' and/or C-10 protected taxane or a mixture of C-7, C-2' and/or C-10 protected taxanes in an organic solvent under an argon atmosphere at low to around room temperature. To this solution is added a base, such as DMAP, TEA, LiOH, Li-t-OBu, n-BuLi, LiH, LiHMDS, KHMDS, K-t-OBu, NaH, NaHMDS, Na-t-Bu or a mixture of any two or more of the foregoing, followed by addition of a t-Boc agent. The mixture is left to react at low to room temperature until complete consumption of the starting material, as visualized by TLC. A solution of an acid, such as AcOH, in an organic solvent is added to the mixture, and the mixture is partitioned between saturated aqueous sodium hydrogen carbonate and mixtures of DCM and ethyl acetate. The combined organic extracts are dried and evaporated to give the crude protected taxane derivative, which can be further purified by column chromatography or crystallized from a suitable solvent.

III. TAXANE STARTING MATERIAL

As noted above, the processes of the present invention may be utilized to convert taxanes of Formula (I), and mixtures of taxanes, into protected taxane derivatives as represented by Formula (II), which can then be used to further synthesize docetaxel. Representative taxanes of Formula (I) include paclitaxel (2), cephalomannine (6), 10-deacetyl taxol (7), 7-xylosyl taxol (8) and 10-deacetyl-7-xylosyl taxol (9). However, other taxanes may also be present in the taxane starting material without affecting the conversion of Formula (I) to Formula (III), as illustrated in Reaction Scheme 1. For example, in addition to one or more taxanes of Formula (I), other taxanes from a crude taxane extract or in a waste taxane solution may also be present in the starting material. These taxanes are a plurality of compounds of a generic tetracyclic baccatin molecular framework as represented by Formula (IV):

wherein $R_A$, $R_B$, $R_C$ and $R_D$ represent substituents which vary between the taxanes. More specifically, $R_A$ is —OH, $R_B$ is —OH or —OAc, $R_C$ is =O, and $R_D$ is —OH or xylosyl. For example, when $R_A$ is —OH, $R_B$ is —OH, $R_C$ is =O and $R_D$ is —OH, the foregoing structure represents 10 deacetylbaccatin III (3), and when $R_A$ is —OH, $R_B$ is —OAc, $R_C$ is =O and $R_D$ is —OH, the foregoing structure represents baccatin III (4), when $R_A$ is —OAc, $R_B$ is —OAc, $R_c$ is —OH, and $R_D$ is —OH, the forgoing structure represents 9-DHB (5).

It is desirable to adjust the amounts of the base and hydroxy protecting in order to fully protect all the reactive hydroxy groups in the taxane starting material before the introduction of the t-Boc group to the nitrogen of the amide group. It can be readily appreciated by one skilled in the art that, in doing so, the t-Boc agent for acylating the amide group is less likely to be consumed by any reactive free hydroxy group.

In certain embodiments, the taxanes utilized in the processes of the present invention may be pure, purified or partially purified taxanes. Such purified and partially purified taxanes may be obtained by any of a number of different methods well known in the art. For example, paclitaxel can be obtained by the methods described in U.S. Pat. No. 6,136,989 to Foo et al. and references incorporated therein.

In other embodiments, the mixture of taxane utilized in the processes of the present invention may be a plurality of taxanes present in a crude taxane extract or in a waste taxane solution or from synthesis. In this way, the disclosed processes may be utilized for high yield and large scale conversion of taxanes present in a waste taxane solution into protected taxane derivatives, which can be used to further synthesize docetaxel. Such waste taxane solutions may comprise (1) pooled waste stream fractions collected following the chromatographic separation and collection of paclitaxel enriched fractions from a crude or partially purified taxane extract, and/or (2) pooled waste mother liquors collected following the recrystallization of a crude or partially purified taxane extract of paclitaxel.

Representative waste taxane solutions may be obtained by a number of different methods, such as, for example, the methods disclosed in U.S. Pat. No. 6,136,989 to Foo et al., and other references cited therein, which patent is incorporated herein by reference in its entirety, and U.S. patent application Ser. No. 10/831,648, which application is assigned to the assignee of the present invention and is incorporated herein by reference in its entirety. A representative method of obtaining a waste taxane solution, which comprises pooled waste stream fractions, comprises the following extraction and column chromatography steps.

Preparation of the Taxane-Containing Material

A suitable taxane-containing material is any tissue that contains a high taxane content. Examples of suitable taxane-containing material include tissues from various species of Yew plants comprising the genus *Taxus*, most preferably the roots and needles of ornamental Yew plants such as *T. canadensis*, *T.×media* spp *Hicksii*, T.×dark green spreader and Hill., *T. chinensis*, *T. wallichiana*, *T. cuspidata*, *T. globosa*, *T. sumatrana*, *T. marei* and *T. floridana*, and the bark of *T. brevifolia* or *T. yunnanensis*. Other suitable material include cultures of plant tissues obtained from a *Taxus* species.

In a typical practice, such as set forth in U.S. Pat. No. 6,139,989, the taxane-containing material is either pulverized, chipped or otherwise ground into small pieces so as to increase efficiency of a solvent extraction. The taxane-containing material may also optionally be dried. Taxane-containing cell culture, cells, microorganisms and fermentation broths will typically be concentrated prior to solvent extraction. Cells and microorganisms can be processed as whole cells or cell paste or pulver.

Extraction

The taxane-containing material may be initially extracted by contacting the material with an organic solvent, usually for a prolonged period of at least 8 hours and typically for about 3 days with or without physical agitation to promote formation of a crude organic extract containing a plurality of taxanes. The extraction may employ any of the solvent systems that are known to be used for the extraction of paclitaxel, including but not limited to, acetone, methanol, ethanol, ethyl acetate, methylene chloride, chloroform, mixtures thereof, and mixtures containing an aqueous component of up to 60%. These solvents are typically added in an amount of about 4-20 liter per kg of the taxane-containing material to prepare the crude organic extract. Reference is made for example, to U.S. Pat. No. 6,136,989 and the publications cited therein which provide a non-exclusive description of several solvent systems that may be used to prepare an organic extract containing a plurality of taxanes.

In one embodiment, the organic solvent is a polar organic solvent, typically an alcohol. For some embodiments, methanol is preferred because of its low cost, ease of removal and efficiency of taxane extraction. In one embodiment, about 6-15 liters of methanol is added for every kg of taxane-containing material to be extracted. The extraction is accelerated by agitating the taxane-containing material, for example, by stirring or percolating the methanol with the taxane-containing material for about 1-5 days at a temperature between room temperature and about 60° C., most typically at about 40° C. When the taxane-containing material contains a paclitaxel content of at least 0.005%, methanol extraction for three days as described above recovers at least 90% of the available paclitaxel from the taxane-containing material, in addition to a plurality of other taxanes, to form a crude methanol extract containing about 0.1-0.5% paclitaxel and having an overall solid content of about 0.5-5% (w/v).

The large volume of methanol extract thus obtained is optionally concentrated, typically about 10-30 fold by evaporation to obtain a methanol extract concentrate having a solid content of about 100-400 g/L.

Liquid-Liquid Extraction

The crude organic extract may be subsequently enriched for taxanes by performing 1-3 liquid-liquid extractions by mixing the organic extract with a non-miscible, organic solvent to form a two phase system wherein one phase contains the plurality of taxanes. Generally, the two phase system includes a polar phase. Optionally, the taxane-containing phase is selected and concentrated by evaporation to form a concentrated extract having a solid content of about 100-400 g/L and a paclitaxel purity of about 1-4%. In some embodiments, water is included to help remove preferentially water soluble materials and the less polar solvent is selected to remove undesirable compounds such as waxes, lipids, pigments, and sterols that are found in different amounts depending on the taxane-containing material used. Typical solvents for liquid-liquid partitioning include hexane, and methylene chloride. Methylene chloride has generally been found to be suitable for liquid-liquid extraction of taxane-containing material especially when the solvent used for the crude organic extract is an alcohol.

The concentrated extract obtained is optionally evaporated and the residue is re-dissolved in a solvent for loading onto a silica chromatography matrix.

Other example methods of performing a liquid-liquid extraction are illustrated in U.S. Pat. Nos. 5,475,120, 5,380,916, and 5,670,673 to Rao and references cited therein, and also in U.S. Pat. Nos. 5,618,538 and 5,480,639 to ElSohly et al. and references cited therein. These methods or variants thereof may alternatively be used in lieu of the embodiments described. Furthermore, liquid-liquid extraction may be omitted altogether when a plant extract containing high taxane levels is obtained by other methods such as for example, by intervening precipitation, crystallization or chromatography steps. One example of such a method is found in PCT Publication Nos. WO 98/07712 by Zamir et al, which uses a precipitation step immediately after obtaining an initial organic extract to obtain a paclitaxel fraction that may be about 1% or higher.

Silica Gel Column Chromatography

As further set forth in U.S. Pat. No. 6,136,989, the concentrated extract may be further purified by normal phase silica chromatography. As used herein, silica chromatography generally refers to the process of contacting a sample dissolved in a feed solvent with a silica matrix then eluting the silica matrix with an eluting solvent to obtain a fraction enriched with a desired component.

The dimensions of the first silica column are selected according to the quantity and purity of the solids to be separated. In one embodiment of a pilot scale process, about 250 grams of solids are dissolved in about 0.75 liters of feed solvent which is then chromatographed over a Silica column of about 1.5-inches×10-feet. In another embodiment, about 40-50 kg of solids are dissolved in about 100-200 liters of feed solvent, and chromatographed over a Silica column of about 18-inches×10-feet.

It has also been shown that a layer of about 1-15 cm of Celite, preferably about 2-8 cm, on top of the silica column is recommended as a column prefilter which substantially decreases the loading time of the sample. It has further been shown that the optimal eluting solvent for the Silica column should be a hexane/acetone mixture at a ratio of about 3:1 or a DCM/ethyl acetate mixture at a ratio of about 7:3. The 'heart cut' fractions containing at least 2% paclitaxel are pooled and further purified, for example, according to the process set forth in U.S. Pat. No. 6,136,989. The remaining waste stream fractions, which contain a plurality of taxanes, including, paclitaxel, 10-deacetylbaccatin III (10-DAB), baccatin III (BACC III), 9-dihydro-13-acetylbaccatin III (9-DHB), cephalomannine, 10-deacetyl taxol (10-DAT), 7-xylosyl taxol and 10-deacetyl-7-xylosyl taxol are pooled into a waste taxane solution for further processing according to the present invention.

Further Purification Steps

As set forth in more detail in U.S. Pat. No. 6,139,989, the paclitaxel enriched 'heart cut' fractions obtained from the foregoing chromatography step may be further purified through one or more additional chromatographic or recrystallization steps. Any waste stream fractions or waste mother liquors collected during such additional purification steps may also be pooled and added to the waste taxane solution for further processing according to the present invention.

IV. PROCESS OF N-DEACYLATION OF THE PROTECTED TAXANE INTERMEDIATE HAVING AN UREA LINKAGE

According to the present invention, a protected taxane of Formula (II) having an urea linkage at the C-3' position further undergoes a N-deacylation step to remove the —C(O)R$^1$ group in the presence of a base. As illustrated in Reaction Scheme 2, a protected docetaxel, as represented by Formula (III) is thus provided:

wherein,
R$^1$ is alkyl, alkenyl or aryl; and
R$^2$, R$^3$ and R$^4$ are the same or different and independently a hydroxy protecting group.

In one embodiment, R$^1$ is phenyl. In another embodiment, R$^1$ is 2-(2-butenyl). In particular, when R$^1$ is 2-(2-butenyl), compound of Formula (II) is a protected cephalomannine, whose subsequent conversion to docetaxel has been described in U.S. application Ser. No. 10/790,622 (hereafter referred as the '622 application). The '622 application is assigned to the assignee of the present invention and is incorporated herein by reference in its entirety.

Suitable base includes metal hydroxide and metal alkoxide. Exemplary base can be, but are not limited to, LiOH, NaOH, Ca(OCH$_3$)$_2$, or NaOCH$_3$. In one embodiment, the base is used in excess in order to avoid hydrolyzing any of the protected hydroxy group. For example, when the base is LiOH, two or more equivalents of LiOH is used. Typically, 5 or more equivalents of LiOH is used, and more typically, 10 or more equivalents of LiOH is used. In a further embodiment, a peroxide can be used in conjunction with the base in the N-deacylation step. Representative peroxide includes, but is not limited to, H$_2$O$_2$, t-butyl hydroperoxide (TBHB) and peroxy acid such as m-chloroperoxybenzoic acid (mCPBA). An exemplary N-deacylation condition includes the use of 20 equivalents of 30% H$_2$O$_2$ with 10 equivalents of LiOH.

After the removal of the —C(O)R$^1$ group, a C-2', C-7 and C-10 protected docetaxel is obtained, as represented by Formula (III). The protected docetaxel can then be subjected to hydrolysis conditions to afford docetaxel.

V. PROCESS FOR PREPARING DOCETAXEL

As noted above, the C-7, C-2' and/or C-10 hydroxy protected taxane derivatives prepared according to the foregoing semi-synthetic processes may be utilized to further synthesize docetaxel. In this regards, in one embodiment, the present invention provides an overall process for preparing docetaxel from paclitaxel, paclitaxel derivative or paclitaxel containing material, the process comprising:

(1) protecting one or more hydroxy groups at the C-2', C-7 and C-10 positions of a compound of Formula (I):

wherein, R$^1$ is alkyl, alkenyl or aryl; and X, Y and Z are the same or different and independently hydroxy or protected hydroxy, to provide a hydroxy-protected taxane intermediate;

(2) introducing a t-Boc group at the nitrogen site of the amide group to provide a protected taxane intermediate with an urea linkage at the C-3' position;

(3) selectively removing the —C(O)R$^1$ group of the protected taxane intermediate with an urea linkage to provide a C-2', C-7 and C-10 protected docetaxel; and (4) converting C-2', C-7 and C-10 hydroxy-protected docetaxel to docetaxel, wherein the step of protecting one or more hydroxy groups at C-2', C-7 and C10 positions and introducing a t-Boc group at the nitrogen site of the amide group of the taxane comprises combining, in a one pot reaction, the taxane of Formula (I) with a base, a hydroxy-protecting group and a t-Boc agent; and wherein the step of removing the —C(O)R$^1$ group of the urea intermediate comprises subjecting the urea intermediate to a base.

In another embodiment, the present invention provides an overall process for preparing docetaxel from an initial mixture of taxanes, wherein the initial mixture comprises paclitaxel, and at least one additional taxane selected from 10-deacetylbaccatin III, baccatin III, cephalomannine, 9-dihydro-13-acetylbaccatin III, 10-deacetyl taxol, 7-xylosyl taxol and 10-deacetyl-7-xylosyl taxol, the process comprising:

protecting the hydroxy groups at the C-7 and C-2' positions of paclitaxel;

introducing a t-Boc group at the nitrogen of the amide group at the C-3' position of paclitaxel to provide a protected paclitaxel derivative having an urea linkage at the C-3' position;

selectively removing the benzoyl group from the urea linkage to provide a protected docetaxel; and converting the protected docetaxel to docetaxel by removing the hydroxy-protecting groups at the C-7, C-2' and C-10 positions, wherein the step of protecting the hydroxy groups at C-2' and C-7 positions, and introducing a t-Boc group at the nitrogen site of the amide group of paclitaxel are carried out in a one pot reaction wherein the mixture containing paclitaxel is combined with a first base, a hydroxy protecting agent and a t-Boc agent; and wherein the step of selectively removing the benzoyl group comprises subjecting the protected paclitaxel derivative having the urea linkage to a second base.

In a further embodiment, the step of protecting the hydroxy groups of paclitaxel further comprises protecting one or more hydroxy groups of each taxanes in the mixture having free hydroxy groups at any of the C-2', C-7 and C-10 positions.

The C-7, C-2' and C-10 protected docetaxel derivatives may be converted to docetaxel by a number of different deprotection methods, such as, for example, the methods disclosed in U.S. patent application Ser. Nos. 10/683,865 and 10/790,622, which applications are assigned to the assignee of the present invention and are incorporated herein by reference in their entireties, and U.S. Pat. Nos. 6,365,750 and 6,307,071, and the references cited therein, which patents and references are incorporated herein by reference in their entireties.

VI. PREPARATION OF DOCETAXEL FROM PRIMARY AMINE DERIVATIVES OF PACLITAXEL

As noted above, the present invention also provides a process for preparing docetaxel via an intermediate of primary amine derivative of paclitaxel. The process can be illustrated in Reaction Scheme 3.

REACTION SCHEME 3

(VI)

reduction (VII)

↓ t-Boc agent docetaxel (1) ←—deprotection—

(VIII)

In particular, a paclitaxel or a derivative thereof as represented by Formula (I) is subjected to nitrosation condition whereby the amide group at the C-3' position is converted to a N-nitrosoamide intermediate, as represented by Formula (V). Suitable nitrosation reagent includes, but is not limited to, $NaNO_2$, $LiNO_2$, $KNO_2$ and other like metal nitrites. Advantageously, an acid, such as acetic acid, is present in the nitrosation step. Alternatively, $N_2O_4$ gas can be used to provide the N-nitrosoamide intermediate.

Under a suitable hydrolysis condition, which typically comprises subjecting the N-nitrosoamide intermediate to a metal hydroxide, or a mixture of metal hydroxide and a peroxide, a N-nitrosoamine intermediate is obtained, as represented by Formula (VI). Representative metal hydroxide includes, but not limited to LiOH and NaOH. Representative peroxide includes, but is not limited to, $H_2O_2$, t-butyl hydroperoxide (TBHB) and peroxy acid such as m-chloroperoxybenzoic acid (mPCBA). In one embodiment, LiOH is used. In another embodiment, a mixture of LiOH and $H_2O_2$ are used.

The nitrosoamine intermediate further undergoes reduction to afford a primary amine derivative of paclitaxel, as represented by Formula (VII). Typical reduction condition includes, but is not limited to Raney nickel, palladium on carbon or platinum on carbon in the presence of hydrogen gas.

Direct conversion of the primary amine derivative of paclitaxel to docetexel can be accomplished according the process as described in the '622 application.

Accordingly, the present invention further provides an alternative overall process of converting a paclitaxel or a derivative thereof to docetaxel comprising:

(1) introducing a nitroso group at the nitrogen of the amide group at the C-3' position of a compound of Formula (I):

(I)

wherein, $R^1$ is alkyl, alkenyl or aryl, and X, Y and Z are the same or different and independently hydroxy or protected hydroxy, to provide a N-nitrosoamide intermediate;

(2) hydrolyzing the N-nitrosoamide intermediate to provide a N-nitrosoamine intermediate;

(3) reducing the N-nitrosoamine intermediate to provide a primary amine intermediate; and (4) converting the primary amine derivative to docetaxel.

Specifically, when $R^1$ is phenyl, the compound of Formula (I) can be paclitaxel, when $R^1$ is 2-(2-butenyl), the compound of Formula (I) can be cephalomannine.

In another embodiment, the present invention provides an overall process for preparing docetaxel from an initial mixture of taxanes, wherein the initial mixture comprises a compound of Formula (I), in particularly, paclitaxel, and at least one additional taxane selected from 10 deacetylbaccatin III, baccatin III, cephalomannine, 9-dihydro-13-acetylbaccatin III, 10-deacetyl taxol, 7-xylosyl taxol and 10-deacetyl-7-xylosyl taxol, the process comprising:

introducing a nitroso group at the nitrogen of the amide group at the C-3' position of a compound of Formula (I):

(I)

wherein, $R^1$ is alkyl, alkenyl or aryl, and X, Y and Z are the same or different and independently hydroxy or protected hydroxy, to provide a N-nitrosoamide intermediate;

hydrolyzing the N-nitrosoamide intermediate to provide a N-nitrosoamine intermediate;

reducing the N-nitrosoamine intermediate to provide a primary amine intermediate; and converting the primary amine derivative to docetaxel.

EXAMPLES

The following Examples disclose a representative process for synthesizing a protected taxane derivative from paclitaxel or paclitaxel containing material, and the subsequent conversion of such derivatives to docetaxel. Unless otherwise noted, all scientific and technical terms have the meanings as understood by one of ordinary skill in the art.

Example 1

Protection of C-7, C-2' and/or C-10 Hydroxy Groups in a One Pot Reaction

Figure 1:
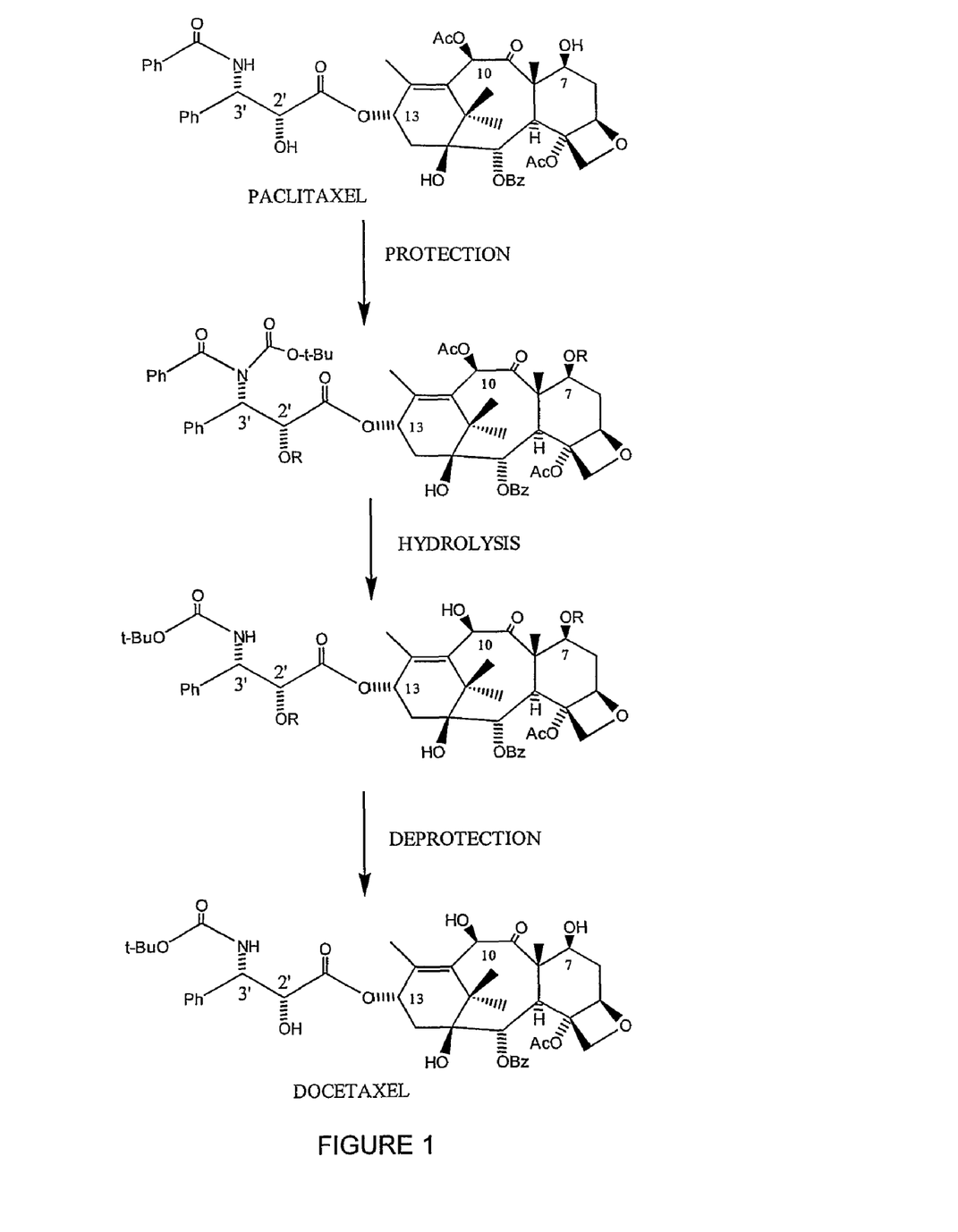
FIG. 1 illustrates a chemical route for the preparation of a protected taxane derivative from paclitaxel or paclitaxel containing material, and the conversion of such derivative to docetaxel according to the present invention.

As shown in FIG. 1, to a stirred solution of paclitaxel or paclitaxel containing material, in an organic solvent, such as THF, at around low to room temperature under an argon atmosphere was treated with a hydroxy-protecting agent, such as $Boc_2O$, dichloroacetyl chloride, acetyl chloride, TESCl or like reagents in the presence of a base, such as 4-(N,N-dimethylamino)pyridine or n-BuLi or a mixture of n-BuLi/Li-t-OBu or like bases. The reaction was stirred at this temperature for a period between 30 minutes to 2 hours until complete consumption of the starting materials, as evidenced by TLC.

Alternatively, to a stirred solution of paclitaxel or paclitaxel containing material, in an organic solvent, such as THF, at around low to room temperature under an argon atmosphere can be treated with a hydroxy-protecting agent such as ethyl vinyl ether, in the presence of a catalytic amount of p-toluenesulfonic acid.

The reaction mixture after the protecting step is used directly in the next step of N-acylation without isolating any of the reaction intermediate.

Preparation of N-acyl Paclitaxel Derivative

To a solution of the C-7, C-2' and/or C-10 protected paclitaxel derivative in an organic solvent, such as the freshly distilled THF, under argon atmosphere at low to around room temperature most preferably at 20° C., was added drop wise a solution of a base, such as DMAP or n-BuLi in hexanes or like bases. After stirring for 30 min to 1 hr at this temperature, a solution of $Boc_2O$ in anhydrous THF was added drop wise to the mixture. The solution was kept at that temperature for an additional 1 to 3 hrs, or until complete consumption of the starting material, as evidenced by TLC, before addition of a solution of an acid in an organic solvent, such as 5% AcOH in THF. The mixture was then partitioned between saturated aqueous sodium hydrogen carbonate and mixtures of dichloromethane and ethyl acetate. Evaporation of the organic layer yielded a crude paclitaxel derivative having an urea linkage, i.e., a paclitaxel N-t-Boc derivative, which could be further purified by either column chromatography or crystallization to yield a pure protected paclitaxel derivative or used directly for the next step in the synthesis.

Alternatively, DMAP (0.1 mmol) was added to a stirred solution of the paclitaxel (1.0 mmol) in dry acetonitrile followed by $BOC_2O$ (1.1 mmol). After stirring for 4 h at room temperature, all starting material was consumed (TLC). The reaction mixture was evaporated at room temperature and the residue partitioned between ether and aqueous $KHSO_4$. The organic extract was thoroughly washed in turn with aqueous solution of $KHSO_4$ and $NaHCO_3$ and finally brine and dried over $MgSO_4$. Evaporation to complete dryness left a light yellow residue that was purified by column chromatography to afford the paclitaxel N-t-Boc derivative.

N-debenzoylation of the Paclitaxel N-t-Boc Derivative

To the above solution in tetrahydrofuran was added a 1.0 N solution of lithium hydroxide. The solution was stirred for 12 h at room temperature. After removal of tetrahydrofuran in vacuo, the basic aqueous residue was acidified by the addition of 10% acetic acid and extracted with ether. Drying ($MgSO_4$) and concentration afforded the crude material that was purified by column chromatography to afford the pure white C-2', C-7 and C-10 protected docetaxel. (Note: The following could also be used: 10 equiv. LiOH, 20 equiv. 30% $H_2O_2$, 3:1 $THF:H_2O$, 0° C.).

Example 2

Synthesis of Docetaxel

As further shown in FIG. 1, C-2', C-7 and C-10 protected docetaxel was hydrolyzed using formic acid to remove the C-7 and/or C-10 t-Boc protecting group and then with a mixture of $NaHCO_3/Na_2CO_3/H_2O_2$ to deprotect the C-2' and/or C-10 acetate groups to yield docetaxel. In the event that the C-2' protecting group is ethoxyethyl, the deprotection is carried out under acidic condition, such as in the presence of acetic acid. Detailed description of deprotection at the C-2', C-7 and C-10 positions are described in U.S. patent application Ser. No. 10/790,622, which application is assigned to the assignee of the present invention and is incorporated herein by reference in its entirety.

Example 3

Synthesis of the Primary Amine Derivative of Paclitaxel

Nitrosation

To a solution of paclitaxel (0.76 mmol) or a paclitaxel containing material in glacial acetic acid (2.5 ml) and acetic anhydride (5 ml) at 0° C. is added $NaNO_2$ (7.6 mmol). The resulting solution can be stirred under argon at 0° C. for 16 h and then poured over ice and extracted with diethyl ether. The combined organic extracts can be washed with water, 5% $Na_2CO_3$, water and saturated NaCl and dried over $MgSO_4$. The dry extracts can be filtered and then concentrated in vacuo, and the crude product is purified by column chromatography using mixtures of hexane-ethyl acetate to afford the pure product.

Hydrolysis

To the above solution in tetrahydrofuran is added a 1.0 N solution of lithium hydroxide. The solution was stirred for 12 h at room temperature. After the removal of tetrahydrofuran in vacuo, the basic aqueous residue can be acidified by the addition of 10% acetic acid and extracted with ether. Drying (MgSO$_4$) and concentration afforded the crude material which can be purified by column chromatography to afford the pure primary amine taxane intermediate. (Note: The following can also be used: 10 equiv. LiOH, 20 equiv. 30% H$_2$O$_2$, in 3:1 THF:H$_2$O)

Reduction

The above hydrolyzed product can then be dissolved in ethanol at room temperature and Raney-Nickel is added in one portion to the stirred solution. The reaction mixture is stirred at this temperature and treated with hydrogen, until the complete consumption of the starting material. The reaction mixture can be filtered and the filtrate evaporated. The residue is then dissolved in an inert solvent such as dichloromethane and worked up as usual. The crude product can be purified by column chromatography using mixtures of dichloromethane and ethyl acetate to afford the pure primary amine derivative of paclitaxel.

Conversion to Docetaxel

The primary amine derivative of paclitaxel (0.091 mmol) can be dissolved in ethyl acetate (9.1 ml) and a saturated solution of NaHCO$_3$ (9.1 ml) was added. To this biphasic mixture Boc$_2$O (0.18 mmol) can be added. The mixture is stirred for 12 h at room temperature and TLC showed complete consumption of the starting material. The reaction can be worked up as usual and the residue purified by column chromatography using mixtures of dichloromethane and ethyl acetate or acetone to give docetaxel.

All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

The invention claimed is:

1. A process comprising:
converting paclitaxel or paclitaxel containing material to docetaxel by protecting a compound of Formula (I):

(I)

wherein R$^1$ is alkyl, alkenyl or aryl; and X, Y and Z are the same or different and independently hydroxy or protected hydroxyl, by:

protecting one or more hydroxyl groups at the C-2', C-7 and C-10 positions of the compound of Formula (I); and introducing a t-Boc group at the nitrogen of the amide group at the C-3' position of the compound of Formula (I) to provide a C-2', C-7 and C-10 and N-t-Boc protected paclitaxel derivative, and converting the one or more hydroxyl groups at the C-2', C-7 and C-10 positions of the compound of Formula (I) to form docetaxel by removing the one or more hydroxy-protecting groups at the C-2, C-7 and C-10 positions, wherein the steps of protecting one or more hydroxy groups and introducing the t-Boc group comprises combining, in a one pot reaction, the compound of Formula (I) with a hydroxyl protecting group and a t-Boc agent.

2. The process of claim 1 wherein the hydroxyl protecting groups at the C-2', C-7 and C-10 positions are the same.

3. The process of claim 1 wherein the hydroxy protecting groups a the C-2', C-7 and C-10 positions are different.

4. The process of claim 1 wherein the step of protecting one or more hydroxy groups at the C-2', C-7 and C-10 positions of the compound of Formula (I) is carried out in the presence of a base.

5. The process of claim 4 wherein the base is DMAP, pyridine, TEA, LION, n-BuLi, LiH1 LiHMDS, KHMDS, NaH, NaHMDS, or a mixture thereof.

6. The process of claim 5 wherein the base further comprises a metal alkoxide, wherein the metal is a Group I, II, III or transition metal.

7. The process of claim 6 wherein the metal alkoxide is Li-t-OBu, Na-t-OBu or K-t-OBu.

8. The process of claim 4 wherein the step of protecting one or more hydroxy groups at the C-2', C-7 and C-10 positions of the compound of Formula (I) comprises combining the compound of Formula (I) with a base and a hydroxy-protecting group in an organic solvent, and wherein the base is DMAP, pyridine, TEA, LiOH, Li-t-OBu, n-BuLi, K-t-OBu or a mixture thereof, and the hydroxy-protecting group is an alkylating agent, silylating agent or acylating agent.

9. The process of claim 8 wherein the hydroxy-protecting group is tert-butoxycarbonyl (t-Boc), benzyloxycarbonyl (CBZ), 2,2,2-trichloroethoxycarbonyl (Troc), 9-fluorenyl methoxycarbonyl (Fmoc), 2,2,2-trichloroethoxymethyl, trimethyl silyl, triethyl silyl, dimethyl(t-butyl)silyl, diethylmethylsilyl, dimethyl phenylsilyl, diphenylmethylsilyl, acetyl, acetoxyacetyl, chloroacetyl, dichloroacetyl, trichloroacetyl or trifluoroacetyl.

10. The process of claim 9 wherein the base is DMAP or n-BuLi and the hydroxy-protecting group is t-Boc, triethylsilyl or dichloroacetyl.

11. The process of claim 1 wherein the step of protecting one or more hydroxy groups at the C-2', C-7 and C-10 positions of the compound of Formula (I) is carried out in the presence of an acid.

12. The process of claim 11 wherein the acid is p-toluenesulfonic acid and the hydroxy protecting group is ethoxyethyl or methoxymethyl.

13. The process of claim 1 wherein the t-Boc agent is BoC2O.

14. A process comprising:
preparing docetaxel from a taxane of Formula (I):

(I)

wherein, R1 is alkyl, alkenyl or aryl; and X, Y and Z are the same or different and independently hydroxy or protected hydroxy, through:
  protecting one or more hydroxy groups at the C-2', C-7 and C-10 positions of the taxane;
  introducing a t-Boc group at the nitrogen of the amide group at the C-3' position of the taxane to provide a protected paclitaxel compound having an urea linkage at the C-3' position;
  selectively removing the —C(O)R1 group from the urea linkage to provide a protected docetaxel; and
  converting the protected docetaxel to docetaxel by removing the hydroxy-protecting groups at the C-2, C-7 and C-10 positions,
  wherein the step of protecting one or more hydroxy groups at C-2', C-7 and C-10 positions, and introducing the t-Boc group at the nitrogen site of the amide group of the taxane comprises combining, in a one pot reaction, the taxane of Formula (I) with a hydroxy protecting agent and a t-Boc agent, and wherein the step of selectively removing the —C(O)R1 group comprises subjecting the protected paclitaxel compound having the urea linkage to a first base.

15. The process of claim 14 wherein the hydroxy protecting groups at the C-2', C-7 and C-10 positions are the same.

16. The process of claim 14 wherein the hydroxy protecting groups at the C-2', C-7 and C-10 positions are different.

17. The process of claim 14 wherein the step of protecting one or more hydroxy groups at the C-2', C-7 and C-10 positions of the taxane is carried out in the presence of a second base.

18. The process of claim 17 wherein the second base is DMAP, pyridine, TEA, LiOH, n-BuLi, LiH, LiHMDS, KHMDS, NaH, NaHMDS, or a mixture thereof.

19. The process of claim 18 wherein the second base further comprises a metal alkoxide, wherein the metal is a Group I, II, III or transition metal.

* * * * *

UNITED STATES PATENT AND TRADEMARK OFFICE
CERTIFICATE OF CORRECTION

PATENT NO. : 7,906,661 B2
APPLICATION NO. : 11/631466
DATED : March 15, 2011
INVENTOR(S) : Ragina Naidu et al.

Page 1 of 1

It is certified that error appears in the above-identified patent and that said Letters Patent is hereby corrected as shown below:

Title Page,

In the List of References Cited at (56), in the continued listing of OTHER PUBLICATIONS, the following reference was omitted from the list and should be included, as follows: --International Search Report dated October 20, 2005 from PCT/US2005/022844--.

In column 8, line 16, the words "TMSC1 (trimethylsilyl chloride), TESC1" should read --TMSCI (trimethylsilyl chloride), TESCI--.

In column 28, line 30, the compound formula "LION" should be --LiOH--.

Signed and Sealed this
Twelfth Day of February, 2013

Teresa Stanek Rea
*Acting Director of the United States Patent and Trademark Office*